(12) United States Patent
Corazzari et al.

(10) Patent No.: US 12,427,237 B2
(45) Date of Patent: Sep. 30, 2025

(54) AIR ELIMINATION DEVICE FOR EXTRACORPOREAL BLOOD TREATMENT

(71) Applicant: B. Braun Avitum AG, Melsungen (DE)

(72) Inventors: Enrico Corazzari, Modena (IT); Alexander Friebe, Recklinghausen (DE); Kai-Uwe Ritter, Melsungen (DE)

(73) Assignee: B. Braun Avitum AG, Melsungen (DE)

( * ) Notice: Subject to any disclaimer, the term of this patent is extended or adjusted under 35 U.S.C. 154(b) by 635 days.

(21) Appl. No.: 17/776,704

(22) PCT Filed: Nov. 19, 2020

(86) PCT No.: PCT/EP2020/082682
§ 371 (c)(1),
(2) Date: May 13, 2022

(87) PCT Pub. No.: WO2021/099463
PCT Pub. Date: May 27, 2021

(65) Prior Publication Data
US 2022/0395619 A1    Dec. 15, 2022

(30) Foreign Application Priority Data
Nov. 19, 2019   (DE) ..................... 10 2019 131 140.3

(51) Int. Cl.
*A61M 1/36* (2006.01)
*A61M 1/16* (2006.01)

(52) U.S. Cl.
CPC ........ *A61M 1/3627* (2013.01); *A61M 1/3644* (2014.02); *A61M 1/16* (2013.01); *A61M 2205/3331* (2013.01)

(58) Field of Classification Search
CPC .... A61M 1/16; A61M 1/3627; A61M 1/3644; A61M 2205/3331
See application file for complete search history.

(56) References Cited

U.S. PATENT DOCUMENTS

| | | |
|---|---|---|
| 5,849,065 A | 12/1998 | Wojke |
| 6,478,962 B1 | 11/2002 | Brockhoff et al. |
| 9,117,012 B2 | 8/2015 | Basaglia |
| 9,474,846 B2 | 10/2016 | Steger |
| 2006/0008380 A1* | 1/2006 | Moozyckine ....... A61M 1/3618 604/4.01 |
| 2008/0171960 A1 | 7/2008 | Brieske et al. |
| 2014/0246373 A1 | 9/2014 | Kopperschmidt |
| 2018/0303995 A1 | 10/2018 | Stange et al. |

FOREIGN PATENT DOCUMENTS

| | | | |
|---|---|---|---|
| DE | 19617036 A1 | 11/1997 | |
| EP | 1203592 B1 | 5/2002 | |
| EP | 2913072 A1 | 9/2015 | |
| FR | 2591899 A1 | 6/1987 | |
| IT | MI20080585 A1 | 10/2009 | |
| JP | 20025177384 A | 6/2002 | |
| JP | 2005261558 A | 9/2005 | |
| JP | 2015058290 A | 3/2015 | |
| JP | 2019054831 A | * 4/2019 | ............ A61M 1/36 |
| JP | 2019083884 A | 6/2019 | |
| WO | 0061208 A1 | 10/2000 | |
| WO | 2004033002 A2 | 4/2004 | |
| WO | 2008053287 A1 | 5/2008 | |

OTHER PUBLICATIONS

Communication received in European Application No. 20 810 937.1-1113 dated Nov. 15, 2024, with translation, 11 pages.
Office Action received in Chinese Application No. 202080090445.7 dated Oct. 24, 2024, with translation, 22 pages.
Search Report received in German Application No. 10 2019 131 140.3 dated Jul. 30, 2020, with translation, 14 pages.
Search Report received in International Application No. PCT/EP2020/082682 dated Feb. 24, 2021, with translation, 5 pages.
Written Opinion received in International Application No. PCT/EP2020/082682 dated Feb. 24, 2021, with translation, 12 pages.
Office Action received in Japanese Application No. 2022-528723 dated Jul. 22, 2024, with translation, 9 pages.
Office Action received in Chinese Application No. 202080090445.7 dated Apr. 8, 2025, with translation, 20 pages.
Office Action received in Japanese Application No. 2022-528723 dated Jan. 27, 2025, with translation, 8 pages.

* cited by examiner

*Primary Examiner* — Krishnan S Menon
*Assistant Examiner* — Tak L Chiu
(74) *Attorney, Agent, or Firm* — Christopher A. Rothe; CM Law

(57) ABSTRACT

A blood circulation system for an extracorporeal blood treatment machine includes: an arterial circulation section; a venous circulation section; a dynamic bubble trap; and an air separator. The blood circulation system conducts blood, during the operation of a blood pump of the extracorporeal blood treatment machine, from a patient to a dialysis unit and from the dialysis unit to the patient. The blood circulation system also includes a recirculation or branch line connected to the bubble trap in order to return part of the blood that flows into the bubble trap into the blood circulation system, upstream of the bubble trap. An extracorporeal blood treatment machine includes the blood circulation system.

11 Claims, 4 Drawing Sheets

AIR ELIMINATION DEVICE FOR EXTRACORPOREAL BLOOD TREATMENT

CROSS-REFERENCE TO RELATED APPLICATIONS

This application is the United States national stage entry of International Application No. PCT/EP2020/082682, filed Nov. 19, 2020, and claims priority to German Application No. 10 2019 131 140.3, filed Nov. 19, 2019. The contents of International Application No. PCT/EP2020/082682 and German Application No. 10 2019 131 140.3 are incorporated by reference herein in their entireties.

FIELD

The disclosure relates to a blood circuit system for an extracorporeal blood treatment machine comprising an arterial line portion, a venous line portion, a dynamic bubble trap, and an air separator, wherein the circuit system is designed to conduct blood from a patient to a dialysis unit and from the dialysis unit to the patient during operation of a blood pump of the extracorporeal blood treatment machine.

BACKGROUND

During blood treatment, in particular a hemodialysis, with a conventional blood treatment machine, blood flowing through a dialysis unit for purification becomes infused with micro air bubbles/microbubbles, which may flow back to the patient without causing an alarm. These microbubbles may deposit in the patient's lungs and also flow through the pulmonary capillaries and may be distributed throughout the body via the arteries, where they can contribute to organ failure. Since the formation of micro air bubbles in the flow through the hemodialysis unit is a common side effect of hemodialysis, it is necessary to separate them from the blood before returning to the patient.

Dynamic bubble traps (DBT) are known for use in heart-lung machines, where they are used to filter out microbubbles for high blood flows/blood flow quantities/blood mass flows. For example, U.S. Pat. No. 6,478,962 B1 discloses such a conventional dynamic bubble trap designed for use in heart-lung machines. The bubble trap accelerates the blood radially as it flows through it, so that the light microbubbles migrate to the region around the central axis of the bubble trap and the heavier blood components are forced radially outward by centrifugal force. The blood that has accumulated in the area around the central axis and which contains the microbubbles is separated from the main blood stream and returned to it.

This is not the case with conventional air separators/gas traps/blood traps used in dialysis units. Depending on the direction/orientation in which the air separator is installed, the air bubbles migrate against gravity to the center or upwards, where they can finally be extracted. This means that the air bubbles essentially only separate due to the difference in density between the air bubbles and the blood. As a result, the level in the chamber of the air separator decreases, which in turn increases the amount of air in the chamber. Such a device for separating air bubbles and blood, conventionally used in dialysis units, is disclosed in WO 2008/53 287 A1. The blood inside the separator flows upward against gravity via a vortex generator, so that the air bubbles collect in an area around the central axis of the separator device. At an upper end of the separator device, the air bubbles are extracted by a vacuum generated by a gas trap.

DE 196 17 036 C2 also shows a device for separating gas bubbles from blood, in which a flow guide component is arranged in the area of an inlet nozzle of the separator device. The flow guide component generates a vortex which forces the blood outward so that the air bubbles remain in the center of the separator device and can be separated.

However, conventional air separators separate (micro) air bubbles particularly well at low blood flows. At higher blood flow quantities, the residence time in the air separator is not sufficient to give the air bubbles sufficient time to rise or, respectively, to accumulate in the center. The effect of the generated vortex is usually present and supports the separation. In addition, it is a disadvantage of conventional air separators that they do not only separate air but also an air-blood mixture.

SUMMARY

The objects and aims of the disclosure are to overcome or at least reduce the disadvantages of the prior art and, in particular, to provide a blood circuit system for an extracorporeal blood treatment machine which ensures an improved process of air separation of microbubbles and thereby excludes or reduces a possible hazard to the patient.

The blood circuit system for the extracorporeal blood treatment machine is thus configured/adapted according to the disclosure to have a branch line or recirculation line connecting the dynamic bubble trap, preferably directly, to the air separator in order to return a portion of the blood flowing into the bubble trap upstream of the bubble trap to the blood circuit system. In other words, after flowing into the bubble trap through the recirculation line and the air separator upstream of the bubble trap, the blood partially flows back into the arterial or venous line portion.

Advantageous embodiments are explained below.

According to the disclosure, the bubble trap may be arranged in the venous line portion so that microbubbles which are hazardous to health and which are formed when flowing through the dialysis unit can be effectively separated from the blood purified in the dialysis unit before it enters the patient.

In a preferred embodiment, the recirculation line of the bubble trap may be fluidically connected to the arterial line portion via the air separator. I.e. the recirculation line is directly connected to the arterial line portion and the air separator is interposed in the recirculation line. Alternatively, it is conceivable that the recirculation line is fluidically connected to an air separator arranged in the arterial line portion. This means that in this case the air separator arranged in the arterial line portion has two blood supply connections, namely one for the arterial line portion and one for the recirculation line as well as a blood discharge connection for the arterial line portion.

In both variants, it is advantageous that no additional conveying means in addition to the conveying means already contained in the system is required to obtain a flow of the fluid/blood/air-blood mixture from the bubble trap through the recirculation line into the arterial line portion. Due to the blood pump already arranged in the blood line, a pressure difference is formed between the arterial and venous line portion, which causes a flow in the recirculation line without separate conveying means and thus at low cost. For sufficient degassing performance, a recirculation rate, i.e. a ratio between a blood flow quantity in the recirculation line and a blood flow quantity in the blood circuit system, of 5-10% is necessary, which determines the constructive/geometric design of the recirculation line. For example, the diameter of the recirculation line can be varied over its length to set the desired recirculation rate.

Alternatively, in another preferred embodiment, the recirculation line can fluidically connect the bubble trap via the air separator with the venous line portion upstream of the bubble trap, i.e. between the dialysis unit and the bubble trap, which leads to an increase in the degassing performance of the bubble trap, since the recirculated blood does not flow through the dialysis unit again and thus no new microbubbles are formed in the recirculated blood. Additionally, in this further preferred embodiment, the recirculation rate can be chosen to be higher, in particular greater than 10%, which in turn improves the degassing performance of the blood trap. Due to the recirculation through the recirculation line, the blood flow quantity in the dynamic bubble trap increases compared to the blood flow quantity set at the blood pump, which also has a positive effect on the degassing performance of the dynamic bubble trap.

Furthermore, the disclosure relates to an extracorporeal blood treatment machine with a blood pump, in which a circuit system according to one of the preceding aspects is insertable, in order to convey blood during operation of the blood pump via the arterial line portion and the venous line portion from a patient to a dialysis unit and from the dialysis unit back to the patient. According to the disclosure, the recirculation line of the circuit system partially returns the blood to the circuit system upstream of the bubble trap after it has flowed into the bubble trap.

In an advantageous embodiment, the recirculation line may be inserted/looped into an additional, second (peristaltic) blood pump, which results in decoupling of the blood flow quantities of the recirculation line and of the arterial or venous line portions. This means that pressure conditions in the recirculation line can be adjusted individually and very precisely to pressure conditions in the arterial and venous line portion. In other words, the blood flow quantity in the recirculation line can be adjusted/controlled by the second blood pump and the blood flow quantity in the arterial and venous line portion by the blood pump of the extracorporeal blood treatment machine.

In addition, it is conceivable according to the disclosure that a (safety) air detector (SAD), preferably designed as an ultrasonic sensor, is arranged downstream of the bubble trap. The air detector may be designed to determine a blood flow quantity. In addition or as an alternative to the air detector, at least one pressure sensor for determining the blood flow quantity may be arranged in the line. According to the disclosure, a conveying capacity, in particular a rotational speed correlating with the conveying capacity, of the blood pump of the extracorporeal blood treatment machine may be determined or set based on the blood flow quantity determined in the air detector and/or in the at least one pressure sensor. In this way, a possible difference in the blood flow quantity can be corrected or compensated for.

BRIEF DESCRIPTION OF THE DRAWING FIGURES

The disclosure is explained in more detail below with the aid of figures based on preferred configuration examples. The following is shown:

The figures are schematic in nature and are merely intended to aid understanding of the disclosure. Identical elements are provided with the same reference signs. The features of the various configuration examples can be interchanged.

DETAILED DESCRIPTION

Figure 1:
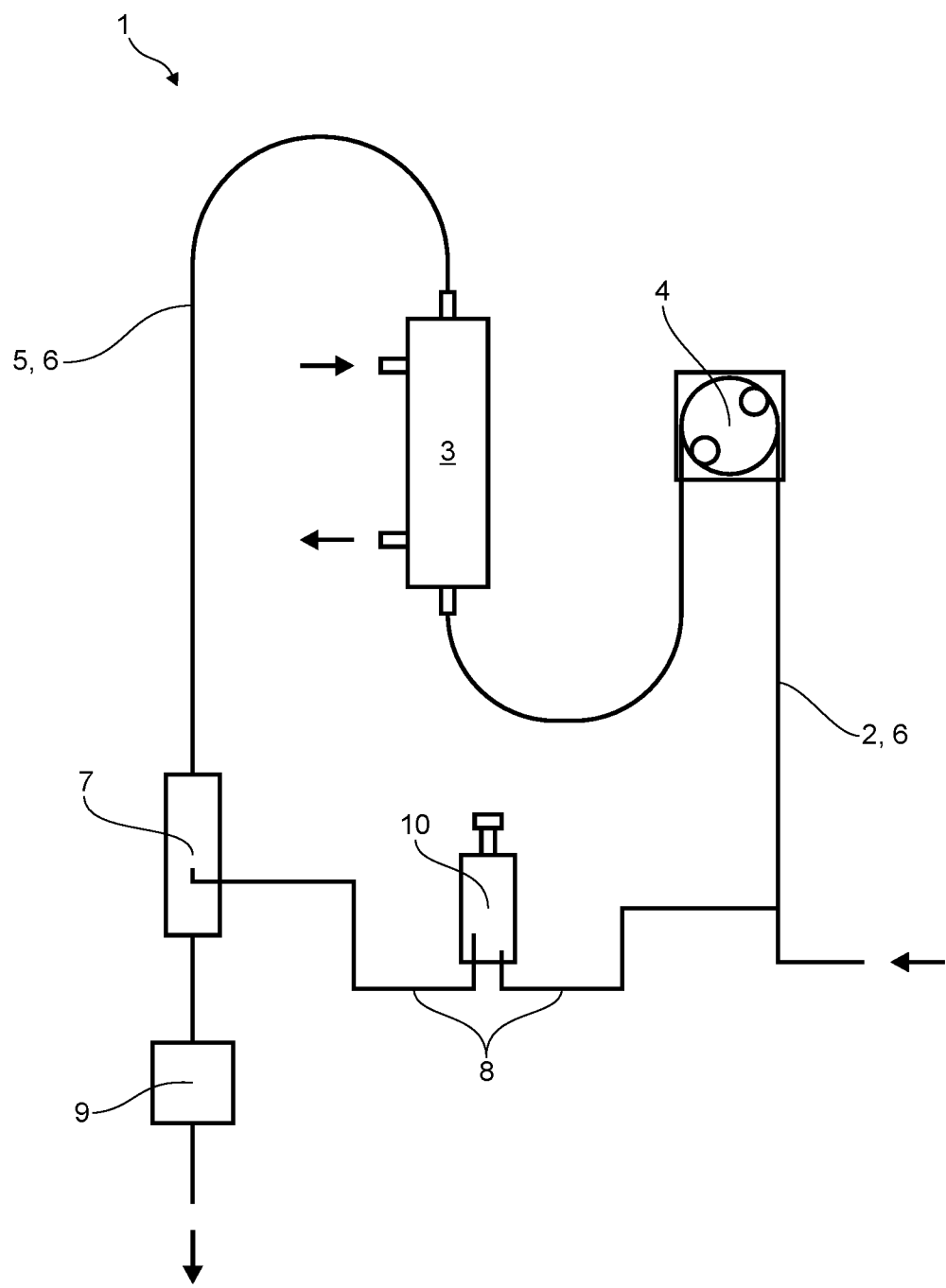
FIG. 1 shows a schematic view of an extracorporeal blood treatment machine with a blood circuit system according to the disclosure according to a first configuration example.

FIG. 1 schematically shows an extracorporeal blood treatment machine 1 according to a first configuration example. The extracorporeal blood treatment machine 1 has an arterial line portion 2 via which blood can flow from a patient to a dialysis unit 3. The dialysis unit 3 is preferably configured as a countercurrent dialyzer, in which blood and dialysate flow past each other, separated by a semipermeable membrane. That is, the dialysate flows through the dialyzer in a direction opposite to the blood flow direction (from top to bottom in FIG. 1). A blood pump 4 in the form of a peristaltic pump is arranged in the arterial line portion 2, which in operation conveys the blood from the patient to the dialysis unit 3. In addition, a venous line portion 5 is arranged in the blood flow direction downstream of the dialysis unit 3, whereby blood purified in the dialysis unit 3 flows back to the patient. According to the disclosure, the arterial line portion 2 and the venous line portion 5 form part of a blood circuit system or of a blood line 6, respectively.

Furthermore, a dynamic bubble trap 7 is arranged in the venous line portion 5. The dynamic bubble trap 7 is designed in such a way that a helix-like flow guide geometry, for example, is arranged inside a tubular housing. When blood flows into the housing of the bubble trap 7, the flow guide geometry generates a vortex/swirl in the blood flow. The vortex generated in this way forces the blood radially outward due to the centrifugal force in the housing. The micro air bubbles, which are lighter than the flowing blood, therefore accumulate in an area around a central axis/axis of rotation of the housing and coalesce to form macro air bubbles. If a pressure difference is applied to a recirculation line 8 arranged in this area, the coalesced macro air bubbles can be separated/discharged via this recirculation line 8.

In order to provide this pressure difference, the recirculation line 8 is connected to the arterial line portion 2 in the first configuration example. In particular, the recirculation line 8 in the first configuration example is connected to the arterial line portion 2 upstream of the blood pump 4. That is, the pressure difference generated by the blood pump 4 between the arterial and venous line portion 2, 5 is used as the pressure difference used for air bubbles separation. The recirculation rate, i.e. the blood flow quantity in the recirculation line 8 relative to the blood flow quantity in the blood line 6, is essentially determined or set by the pressure difference applied to the recirculation line 8. For sufficient degassing performance, a recirculation rate of approx. 5-10% is necessary. The necessary recirculation rate thus decisively defines the geometric configuration/design of the recirculation line 8. In other words, the diameter of the recirculation line 8 has to be varied over its length in such a way that the recirculation rate is 5-10% depending on the pressure difference applied.

When using the bubble trap 7 to separate air bubbles, however, not only air bubbles flow into the recirculation line 8. Rather, an air-blood mixture is sucked into the recirculation line 8 by the pressure difference applied to the recirculation line 8.

In addition, an air detector 9 is arranged in the extracorporeal blood treatment machine 1 downstream of the bubble trap 7. This air detector 9 is configured as an ultrasonic sensor and monitors the presence of air bubbles in the purified blood before it is returned to the patient. In the first configuration example, the air detector 9 is additionally used to determine/measure a blood flow quantity. Based on this measured blood flow quantity, a conveying capacity of the blood pump 4 is set. In particular, the conveying capacity of the blood pump 4 is set via a rotational speed of the blood pump 4 correlating with the conveying capacity. That is, by measuring the blood flow quantity in the air detector 9 and setting the rotational speed of the blood pump 4, the aforementioned difference between the blood flow quantity supplied to the patient and the blood flow quantity withdrawn from the patient is corrected or compensated for, respectively. In other words, the rotational speed of the blood pump 4 is corrected so that a blood flow quantity desired for the blood treatment is achieved as an effective blood flow quantity. In addition to the blood flow quantity measured in the air detector 9, pressure values detected in the arterial line portion 2 and/or the venous line portion 5 can alternatively or additionally be used to determine and correct the effective blood flow quantity.

As can be seen in FIG. 1, in the first configuration example, an air separator 10 is arranged in the recirculation line 8, which additionally increases the degassing performance of the extracorporeal blood treatment machine 1. The air separator 10 is supplied with the air-blood mixture flowing in the recirculation line 8, so that the macro air bubbles remaining in the air-blood mixture can be isolated/separated within the air separator 10.

Figure 2:
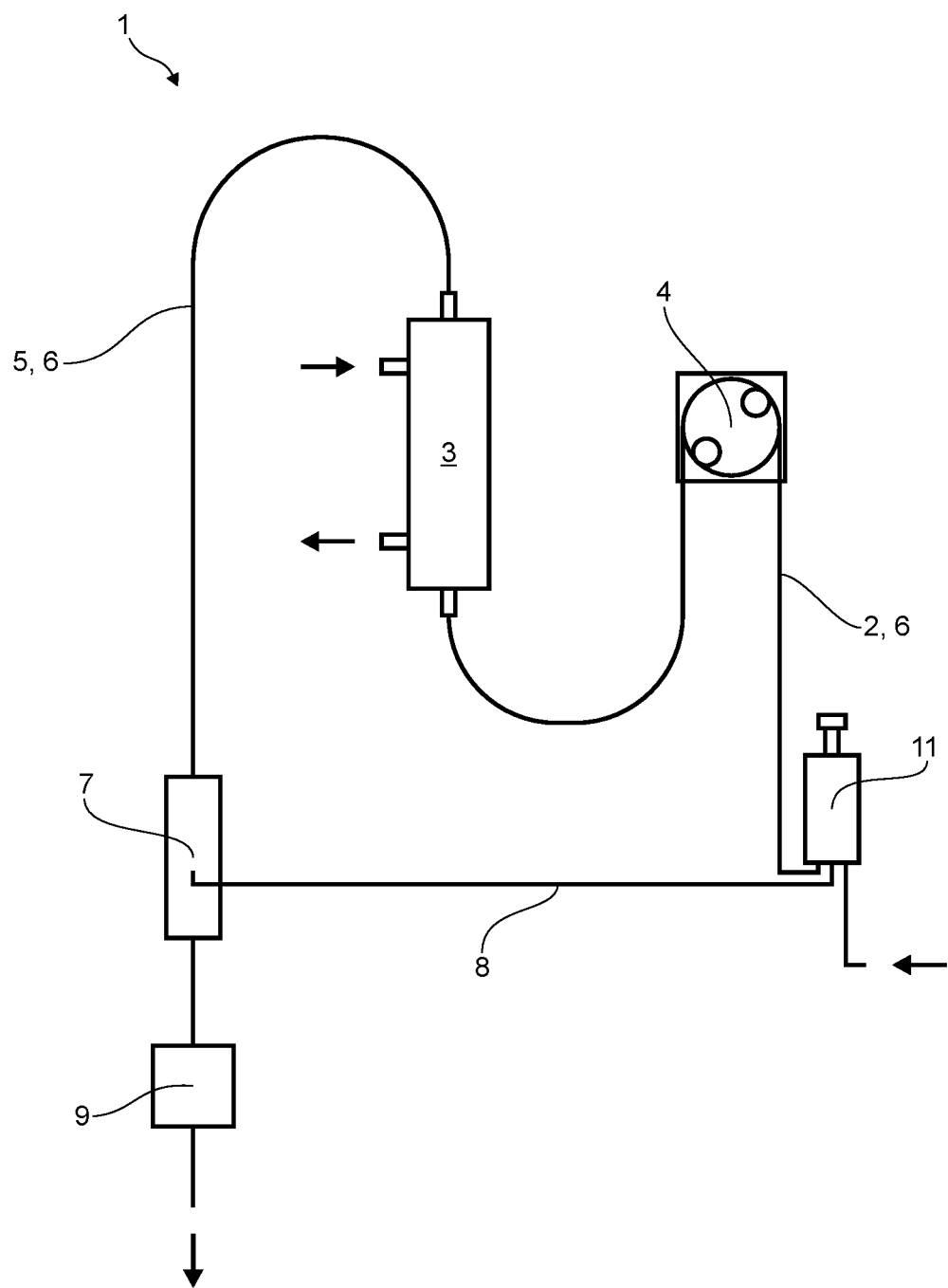
FIG. 2 shows a schematic view of an extracorporeal blood treatment machine with a blood circuit system according to the disclosure according to a second configuration example.

FIG. 2 shows the extracorporeal blood treatment machine 1 according to a second configuration example. In the description of the extracorporeal blood treatment machine 1 according to this second configuration example, only the differences from the first configuration example are described below.

As can be seen in FIG. 2, in the extracorporeal blood treatment machine 1 according to the second configuration example, the air separator 10 is not arranged in the recirculation line 8. Rather, an (existing) arterial air separator 11 is fluidically connected to the recirculation line 8 and the dynamic bubble trap 7 via an additional connection.

Figure 3:
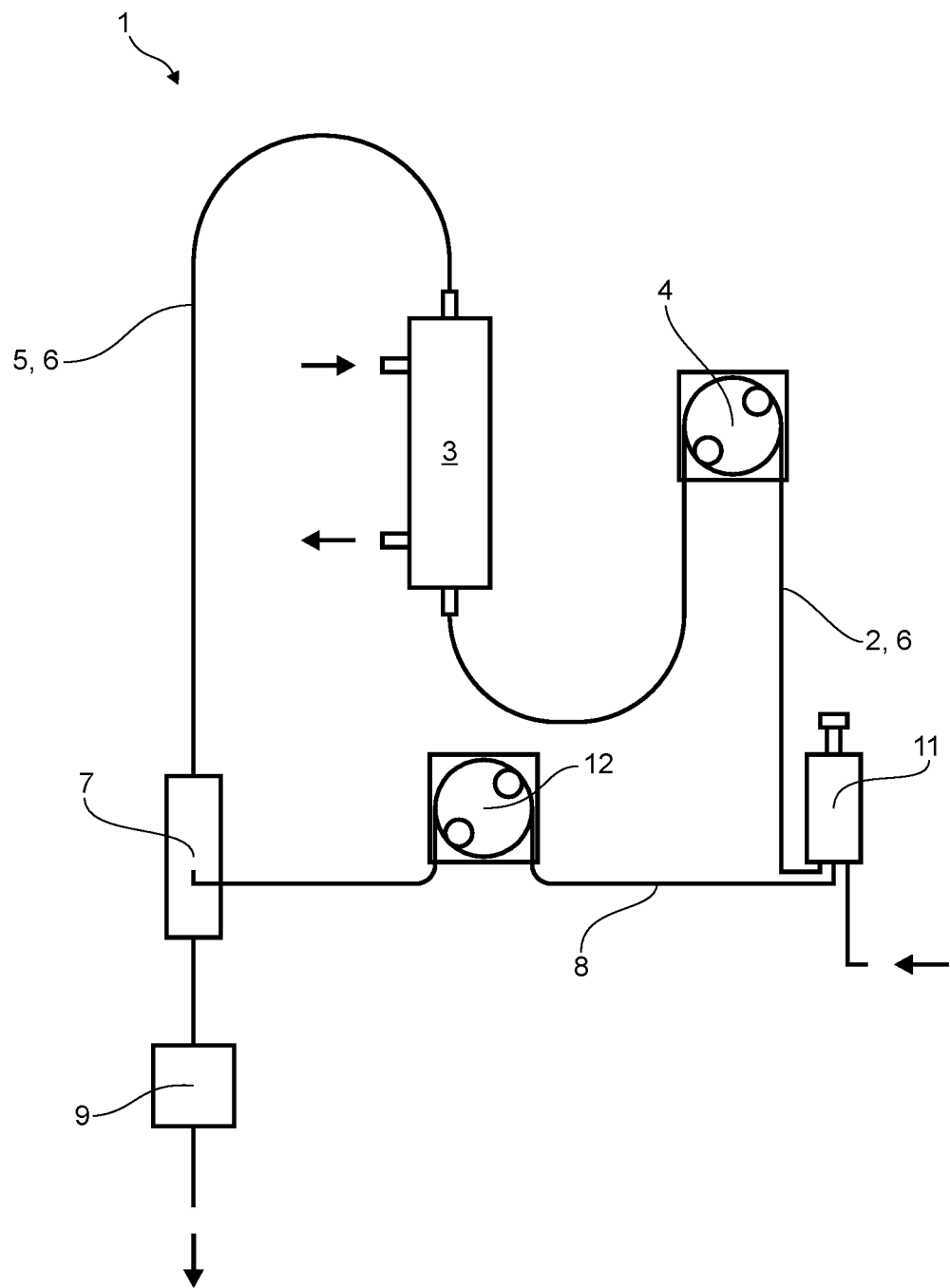
FIG. 3 shows a schematic view of an extracorporeal blood treatment machine with a blood circuit system according to the disclosure according to a third configuration example.

As a further variant of the second configuration example shown in FIG. 2, FIG. 3 shows the extracorporeal blood treatment machine 1 according to a third configuration example. Here, a second peristaltic blood pump 12 is interposed between the bubble trap 7 and the arterial air separator 11 in the recirculation line 8. Thus, the pressure difference across the recirculation line 8 and thus the recirculation rate can be essentially decoupled from the blood flow in the blood line 6 and can be very precisely set largely independently of it. In other words, the pressure ratios in the recirculation line 8 can be individually adapted to the pressure ratios in the arterial and venous line portion 2, 5.

Figure 4:
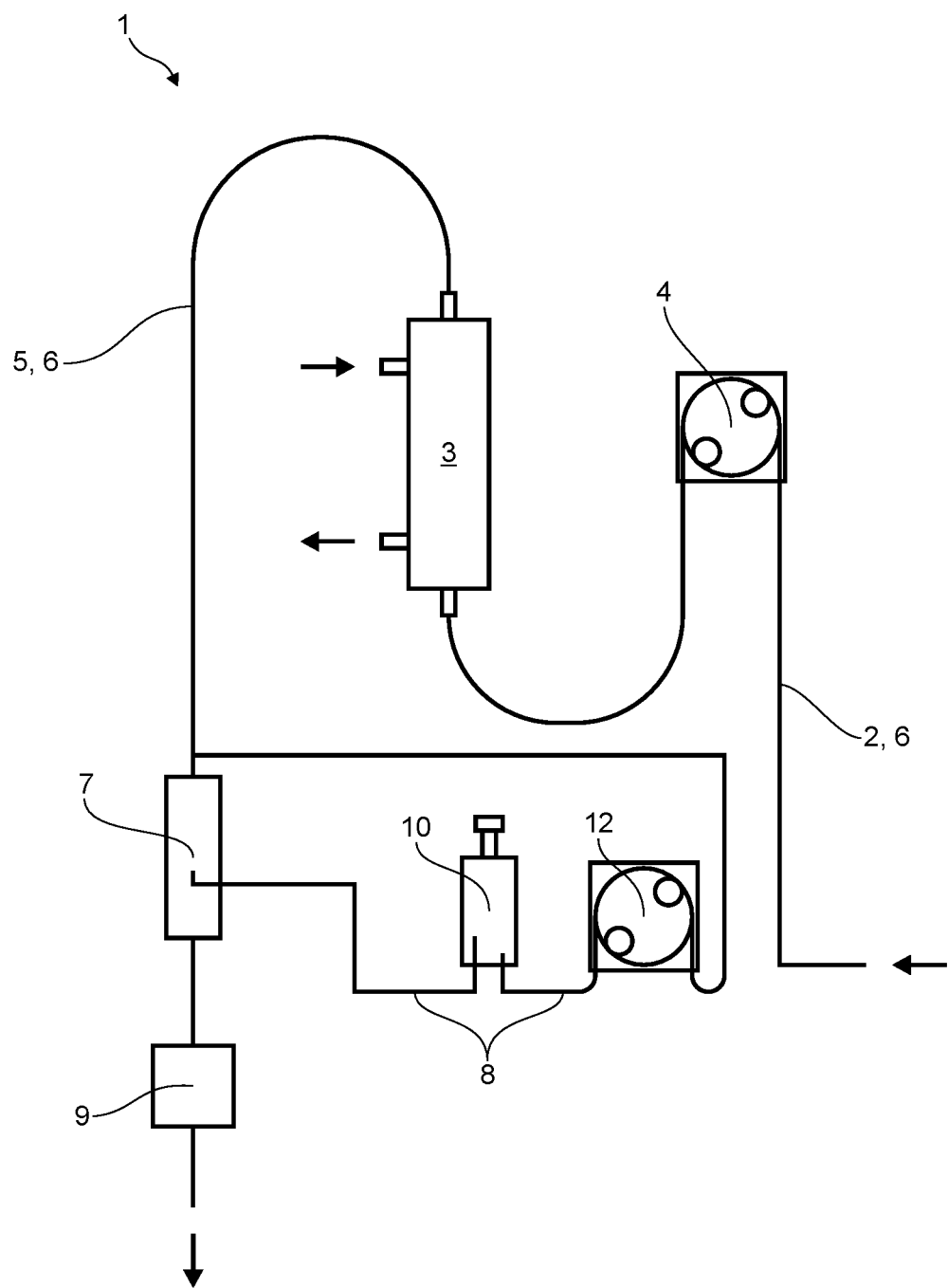
FIG. 4 shows a schematic view of an extracorporeal blood treatment machine with a blood circuit system according to the disclosure according to a fourth configuration example.

Similarly, in the extracorporeal blood treatment machine 1 shown in FIG. 4 according to a fourth configuration example, the second blood pump 12 is arranged in the recirculation line 8. However, in the fourth configuration example, the recirculation line 8 is not connected to the arterial air separator, but the air-blood mixture flowing out of the bubble trap 7 into the recirculation line 8 is fed back to the blood line 6 in the venous line portion 5 upstream of the bubble trap 7. In order to separate the air bubbles remaining in the air-blood mixture, the air separator 10 and the second blood pump 12 are arranged in the recirculation line 8. That is, after flowing through the bubble trap 7, the recirculation line 8 and the air separator 10, the recirculated air-blood mixture is returned to the venous line portion 5 upstream of the bubble trap 7, so that any air bubbles remaining in the recirculated air-blood mixture are again supplied to the bubble trap 7, resulting in a higher degassing performance of the bubble trap 7. In other words, in the fourth configuration example, the recirculation line 8 connects the bubble trap 7 to the venous line portion 5 upstream of the bubble trap 7, i.e. between dialysis unit 3 and bubble trap 7. In this case, the air separator 10 and the second blood pump 12 are arranged in the recirculation line 8, so that the recirculation rate in the recirculation line 8 is determined by the second blood pump 12.

The fact that the air-blood mixture in the fourth configuration example is again fed to the bubble trap 7 without flowing through the dialysis unit 3 further increases the degassing performance without causing additional purification losses in the dialysis unit 3. In this case, the recirculation rate can be selected to be higher than in the further configuration examples, in particular greater than 10%, since there is no loss of purification effect. As the recirculation rate increases, the degassing performance of the bubble trap 7 improves, since the vorticity of the vortex generated in the bubble trap 7 increases at higher mass flows (blood flow quantities) and the microbubbles are thus separated more effectively.

The invention claimed is:

1. A blood circuit system for an extracorporeal blood treatment machine comprising an arterial line portion, a venous line portion, a dynamic bubble trap, and an air separator, wherein the blood circuit system is designed to conduct blood from a patient to a dialysis unit and from the dialysis unit to the patient during operation of a blood pump of the extracorporeal blood treatment machine, the blood circuit system further comprising a recirculation line connecting the dynamic bubble trap to the air separator in order to return a portion of blood flowing into the dynamic bubble trap back to the blood circuit system at a location upstream of the dynamic bubble trap, wherein the air separator is located downstream from the dynamic bubble trap along the recirculation line.

2. The blood circuit system according to claim 1, wherein the dynamic bubble trap is arranged in the venous line portion.

3. The blood circuit system according to claim 1, wherein the recirculation line fluidically connects the dynamic bubble trap to the arterial line portion via the air separator.

4. The blood circuit system according to claim 1, wherein the recirculation line is fluidically connected to the air separator arranged in the arterial line portion.

5. The blood circuit system according to claim 1, wherein the recirculation line fluidically connects the dynamic bubble trap via the air separator to the venous line portion at a location between the dialysis unit and the dynamic bubble trap.

6. An extracorporeal blood treatment machine comprising a blood pump adapted to receive the blood circuit system according to claim 1 in order to convey blood during operation of the blood pump via the arterial line portion and the venous line portion from the patient to the dialysis unit and from the dialysis unit back to the patient, wherein the recirculation line partially returns a quantity of blood back to the blood circuit system at a location upstream of the dynamic bubble trap, after the quantity of blood has flowed into the dynamic bubble trap.

7. The extracorporeal blood treatment machine according to claim 6, wherein the recirculation line is inserted into an additional blood pump.

8. The extracorporeal blood treatment machine according to claim 6, wherein an air detector is arranged downstream of the dynamic bubble trap and is designed to determine a blood flow quantity.

9. The extracorporeal blood treatment machine according to claim 8, further comprising at least one pressure sensor for determining the blood flow quantity.

10. The extracorporeal blood treatment machine according to claim 9, wherein a conveying capacity of the blood pump is determined based on the blood flow quantity determined in the air detector and/or in the at least one pressure sensor.

11. The extracorporeal blood treatment machine according to claim 1, wherein the dynamic bubble trap is located in the venous line portion downstream of the dialysis unit and at least a portion of the recirculation line is located between the dynamic bubble trap and the air separator, such that an entire quantity of blood flowing out of the dialysis unit passes into the dynamic bubble trap, and only the portion of blood flowing from the dialysis unit into the dynamic bubble trap passes through the recirculation line to the air separator, and a remaining portion of blood flowing from the dialysis unit into the dynamic bubble trap does not pass through the recirculation line to the air separator.

* * * * *